US010064907B2

(12) United States Patent
    Campmany

(10) Patent No.: US 10,064,907 B2
(45) Date of Patent: Sep. 4, 2018

(54) PROCESS TO IMPROVE FEED EFFICIENCY AND CARCASS CHARACTERISTICS OF ANIMALS

(71) Applicant: Joan Torrent Campmany, Cary, NC (US)

(72) Inventor: Joan Torrent Campmany, Cary, NC (US)

(73) Assignee: Oligo Basics Agroindustrial LTDA., Cascavel, PR (BR)

( * ) Notice: Subject to any disclaimer, the term of this patent is extended or adjusted under 35 U.S.C. 154(b) by 340 days.

(21) Appl. No.: 14/756,229

(22) Filed: Aug. 19, 2015

(65) Prior Publication Data

US 2015/0359831 A1   Dec. 17, 2015

Related U.S. Application Data

(63) Continuation-in-part of application No. 13/385,521, filed on Feb. 23, 2012, now abandoned.

(51) Int. Cl.

| | |
|---|---|
| A61K 36/22 | (2006.01) |
| A61K 31/231 | (2006.01) |
| A61K 31/05 | (2006.01) |
| A61K 31/192 | (2006.01) |
| A61K 31/23 | (2006.01) |
| A23K 20/158 | (2016.01) |
| A23K 20/10 | (2016.01) |
| A23K 50/10 | (2016.01) |
| A23K 50/75 | (2016.01) |
| A23K 50/30 | (2016.01) |
| A23K 50/60 | (2016.01) |

(52) U.S. Cl.
CPC .............. *A61K 36/22* (2013.01); *A23K 20/10* (2016.05); *A23K 20/158* (2016.05); *A23K 50/10* (2016.05); *A23K 50/30* (2016.05); *A23K 50/60* (2016.05); *A23K 50/75* (2016.05); *A61K 31/05* (2013.01); *A61K 31/192* (2013.01); *A61K 31/23* (2013.01); *A61K 31/231* (2013.01)

(58) Field of Classification Search
None
See application file for complete search history.

(56) References Cited

U.S. PATENT DOCUMENTS

| | | |
|---|---|---|
| 4,670,469 A | 6/1987 | Schewe et al. |
| 5,427,802 A | 6/1995 | Evans et al. |
| 5,725,894 A | 3/1998 | Toyomizu et al. |
| 5,776,919 A | 7/1998 | Sukigara et al. |
| 6,022,566 A | 2/2000 | Miller |
| 6,379,694 B1 | 4/2002 | Hatano et al. |
| 8,377,485 B2 | 2/2013 | Campmany |
| 2006/0140881 A1 | 6/2006 | Xu et al. |
| 2006/0204453 A1 | 9/2006 | Ginger |
| 2008/0226760 A1 | 9/2008 | Campmany |
| 2011/0250303 A1 | 10/2011 | Nagashima et al. |

FOREIGN PATENT DOCUMENTS

| | | |
|---|---|---|
| JP | 403240721 A | 10/1991 |
| WO | WO 93/22936 | 11/1993 |

OTHER PUBLICATIONS

Gellerman et al., "Antimicrobial effects of anacardic acids," Canadian Journal of Microbiology, vol. 15, pp. 1210 1223 (1969).
Eichbaum, "Biological Properties of Anacardic Acid (O-Penta-Decadienyl-Salicylic Acid) and Related Compounds," Mem. Inst. Butantan, vol. 19, pp. 71-96 (1946).
Novak et al., "Antimicrobial Activity of Some Ricinoleic and Oleic Acid Derivatives," Journal of the American Oil Chemists Society, vol. 38, pp. 321-324 (1961).
Stewart et al., "Inhibitory Actions of Laxatives on Motility and Water and Electrolyte Transport in the Gastrointestinal Tract", Journal of Pharmacology and Experimental Therapeutics, vol. 192, pp. 458-467 (1975).
Ammon et al., "Effects of Oleic and Ricinoleic Acids on Net Jejunal Water and Electrolyte Movement," Journal of Clinical Investigation, vol. 53, pp. 374-379 (1974).
Gaginella et al., "Castor Oil: New Lessons from an Ancient Oil," Phytotherapy Research, vol. 12, pp. S128-S130 (1998).
Toyomizu et al., "a-Glucosidase and Aldose Reductase Inhibitors: Constituents of Cashew, Anacardium occidentale, Nut Shell Liquids", Phytotherapy Research, vol. 7, pp. 252-254 (1993).
Vieira et al., "Pro-and anti-inflammatory actions of ricinoleic acid: similarities and differences with capsaicin", Naunyn-Schmiedeberg's Arch Pharmacol, vol. 364, pp. 87-95 (2001).
Trevisan et al., "Charaterization of alkyl phenols in cashew (*Anacardium occidentale*) products and assay of their antioxidant capacity", Food and Chemical Toxicology, vol. (?), pp. 1-10 (2005).
Purevjav et al., "Effects of functional oils and monensin on cattle finishing programs", The Professional Animal Scientist, vol. 29, pp. 426-434 (2013).
Goodrich et al., "Influence of Monensin on the Performance of Cattle", Journal of Animal Science, vol. 58, pp. 1484-1498 (1984).
Perry et al., "Effect of Monensin on Beef Cattle Performance", Journal of Animal Science, vol. 42, pp. 761-765 (1976).
Montgomery et al., "Effects of dietary zilpaterol hydrochloride on feedlot performance and carcass characteristics of beef steers fed with and without monensin and tylosin", American Society of Animal Science, vol. 87, pp. 1013-1023 (2009).

*Primary Examiner* — Susan Hoffman
(74) *Attorney, Agent, or Firm* — Baker Donelson, PC; Emily R. Billig; Thomas Hodge

(57) ABSTRACT

This invention relates to a process to improve the feed efficiency and carcass characteristics of (1) animals that are not showing clinical signs of disease or other microbial challenge and (2) animals that are not expected to show clinical signs of disease or other microbial challenge (that is, within the next 1-2 weeks or less) because of known management practices, such as weaning of piglets. The process of this invention can be used to decrease the cost of animal diets, to improve performance of animals and to improve the percentage of carcass in animals.

33 Claims, No Drawings

PROCESS TO IMPROVE FEED EFFICIENCY AND CARCASS CHARACTERISTICS OF ANIMALS

CROSS REFERENCE TO RELATED APPLICATIONS

This application is a continuation-in-part, of, and claims the benefit of, U.S. Ser. No. 13/385,521, filed Feb. 23, 2012, now abandoned.

STATEMENT REGARDING FREQUENTLY SPONSORED RESEARCH OF DEVELOPMENT

Not applicable

TECHNICAL FIELD

This invention relates to a process that improves the feed efficiency of animals. The process of this invention can be used to improve the feed efficiency of many types of animals and, therefore, is useful to decrease feed costs for animals and also as a growth promoter or enhancer.

BACKGROUND OF THE INVENTION

The cost of feeding an animal is estimated to be approximately 70% of the total cost of the production of that animal. Therefore, ways to decrease these feeding costs can have a very important effect on the final cost of animal products, such as meat, milk, eggs and wool.

Animals use the energy extracted from the feed for different purposes. A principal purpose is referred to as "maintenance". The energy for maintenance is used by the animals to maintain life. If the feed does not provide enough energy for maintenance, animals lose weight as they have to use their body reserves to survive. Once maintenance requirements have been met, the rest of the energy can be used for growth (for example, meat, milk, eggs and wool) or reproduction.

There are two classical ways to increase the amount of energy that animals are able to extract from feed and, therefore, to improve their energy and/or feed efficiency. One is to increase the energy in the feed, and the other is to change the energy metabolism of the animal to make their metabolism more efficient.

Enzymes increase the energy of the feed. The idea behind the use of enzymes is that enzymes degrade compounds that are undigestible or have antinutritional properties. This degradation allows the animal to extract more energy from the feed. Typical examples of enzymes are pentosanases, beta-glucanases or phytases used to degrade pentosans (found in wheat), beta-glucans (found in barley) or phytates (found in vegetable ingredients), respectively.

Antibiotics change the way energy is used by the animal. The exact way that antibiotics increase the energy available for the animal is not clearly understood. However, antibiotics have been related to a decrease in the amount of energy needed by the animal to fight pathogens. Antibiotics would keep the microbial challenge low and, as a result, less energy would be allocated to the immune system to fight those pathogens. This savings in energy can then be used for production. Therefore, antibiotics would not increase the energy density of the feed, but would decrease the maintenance requirements of the animal, with the net result being more energy available for production.

New regulatory measures are constraining the use of antibiotics as growth promoters in many countries. In 2006, the European Union forbade the use of antibiotics as growth promoters, and the FDA is studying limitations on the use of antibiotics in the U.S.

Hormones are examples of other products that change the way energy is used by animals by changing where that energy is directed. For example, the hormone somatotropin increases the amount of energy allocated to milk production instead of meat production. The hormone ractopamine increases the amount of lean tissue which correspondingly decreases the amount of fat tissue.

The use of hormones and antibiotics in animal production is facing a strong opposition by public opinion due to possible residues of these materials in animal products. Therefore, products that could improve feed and energy efficiency that are not hormones or antibiotics have a very attractive market.

U.S. Patent Application Publication No. US 2008/0226760 discloses a composition which is useful in the process of this invention. However, that composition is disclosed as having antimicrobial activity; that is, for animals that show clinical signs of disease or other microbial challenge.

In the process of this invention, the composition disclosed in U.S. Patent Application Publication No. US 2008/0226760 is shown to improve feed efficiency for animals kept in situations free of disease or other microbial challenge. Therefore, the improved feed efficiency results from a change in the use of energy from feed, not from a decrease in the microbial challenge.

The present invention shows that the improved energy efficiency of animals treated with this composition occurs when the animals are kept in situations free of disease or other microbial challenge. Therefore, the improved energy efficiency is not caused by the decrease in microbial challenge or the lower amount of energy used by the immune system, but by changes in the use of energy. Thus, in the present invention, a process has been developed:
- to improve the energy efficiency of animals;
- to improve the carcass characteristics of animals;
- to decrease the cost of feeding animals;
- to not leave residues in the meat, milk, eggs, wool or other products of animals.

SUMMARY OF THE INVENTION

Briefly described, this invention provides a process that can be used to improve the feed efficiency and carcass characteristics of animals. This process can be used in foods for various types of animals. This process does not leave toxic residues in food or in the carcass of animals.

The process of this invention is directed to (1) animals that are not showing clinical signs of disease or other microbial challenge and (2) animals that are not expected to show clinical signs of disease or other microbial challenge in the near future (that is, within the next 1-2 weeks or less) because of known management practices, such as weaning of piglets.

In this application, the term "clinical signs" will be understood to mean objective parameters which are visual and/or measurable. Examples of clinical signs are fever, diarrhea and decreases in feed intake.

There are no known adverse or side effects of animals treated by the process of this invention, which can be used during the life of the animals.

These and other features and advantages of this invention will become apparent from the following detailed description.

DETAILED DESCRIPTION OF THE INVENTION

In accordance with this invention, a process is provided in which an animal that does not show clinical signs of disease or other microbial challenge is treated with a composition which comprises:

A. from about 2.0 to about 76.0 percent by weight of at least one triglyceride containing at least one hydroxylated fatty acid having from about 10 to about 20 carbon atoms in its chain and B. from about 24.0 to about 95.0 percent by weight of cashew nut shell liquid or a compound selected from the group consisting of cardol, cardanol, anacardic acid and salts of anacardic acid, wherein the feed efficiency and carcass characteristics of the animal are improved in comparison to the animal before treatment.

Ricinoleic acid has been shown to have antimicrobial (Novak et al, 1961, *J. Amer. Oil Chem. Soc.* 38:321-324) and anti-inflammatory (Vieira et al., 2001, *Naunyn-Schmiedeberg's Arch. Pharmacol.*, 364:87-95) activities, but an effect on the energy usage or feed efficiency of an animal has not been reported.

The liquid from the cashew nut shell and its components have been shown to have multiple activities, such as antimicrobial (Eichbaum, 1946, *Mem. Inst. Butantan,* 19:71-96; Gellerman et al., 1969, *Can. J. Microbiol.* 15: 1219-1223) and antioxidant (Trevisan et al., 2006, *Food Tech. Toxicol.* 44(2):188-97), as well as inhibition of the enzymes alpha glucosidase, invertase and aldose reductase (Toyomizu et al., 1993, *Phytotherapy* 7, 252-254). However, an effect on the energy efficiency of an animal has not been reported.

The effects of one of the components of the cashew nut shell liquid on feed efficiency of animals was done in rats supplemented with anacardic acid and showed no differences between supplemented and non-supplemented animals (Toyomizu et al., 2003, *Anim. Sci. J.,* 74: 499-504).

As defined above, the process of this invention utilizes a composition having 2 essential components, the first of which is at least one triglyceride containing at least one hydroxlated fatty acid which has from about 10 to about 20 carbon atoms in its chain. This component is used in an amount of about 2.0 to about 76.0 percent by weight based on the weight of the composition, preferably about 10.0 to about 30.0 percent by weight.

As used in this application, the term "weight percent" or "percent by weight" is based on the weight of the total composition.

Examples of triglycerides for use in this process include castor oil and bladderpod oil. The preferred triglyceride is castor oil. The composition may contain a blend of two or more triglycerides.

Preferred hydroxylated fatty acids include ricinoleic acid, hydroxystearic acid and lesquerolic acid. The triglyceride may contain more than one hydroxylated fatty acid.

The second essential component is the cashew nut shell liquid (that is, the liquid derived from the cashew nut shell) or at least one compound derived from the cashew nut shell liquid. These compounds (also referred to as cashew nut shell compounds) are cardol, cardanol, anacardic acid and salts of anacardic acid. The composition may contain more than one cashew nut shell compound. This component is used in an amount of about 24.0 to about 95.0 percent by weight based on the weight of the composition, preferably about 30.0 to about 80.0 percent by weight.

Examples of anacardic acid salts which can be used in the process of this invention are the zinc and copper salts.

Preferably, the ratio of triglyceride:cashew nut shell component (whether the liquid or one or more compounds) is from about 1:4 to about 1:2, most preferably 1:3.3.

This invention provides a process that improves the feed efficiency and carcass characteristics of an animal independently of the antimicrobial activity of the animal. This invention has shown beneficial effects when animals were in situations where no microbial challenge was taking place, and/or when compared to animals fed antimicrobial compounds.

Although not clearly understood, the advantages of this process are believed to result from a decrease in the maintenance requirements of the animal through a decrease in the visceral organ mass of the treated animals. Visceral organs (such as the liver and intestines) are highly active and use a lot of energy. A process that decreases the energy used by the visceral organs, either through a decrease in organ size or energy use, frees more energy for growth or the production of products (such as meat, milk, eggs and wool). The decrease in visceral organ mass also results in improvements of the carcass characteristics, as the percentage of saleable meat in proportion to the total weight of the animal is increased, resulting in an improvement of the economic value of the treated animal.

The compositions for use in this process may be applied directly, or through solid and liquid carriers, to facilitate the application of the composition. Appropriate carriers are those that do not interfere with the release of the essential components.

The administration of the composition will vary in accordance to the user's objective. However, the dose must be between about 10 and about 10,000 ppm, in proportion to the total (or complete) animal feed ingested by the animal or offered to the animal. A preferred dose is from about 250 to about 2,000 ppm.

In the process of this invention, the composition is added to the animal feed. Stated another way, the animal feed is supplemented by the composition. The composition does not replace the animal feed.

Other components can be used in the composition to achieve various effects and/or to enhance the performance of the process. Examples of such optional components include carriers, thickening agents, preservatives, perfumes, stabilizing agents, organic acids and emulsifiers. If used, these components are used in amounts necessary to achieve their purpose, but not in amounts which would adversely affect the process.

Examples of such optional components are expanded vermiculite, fats, ethanol, glycerol and propylene glycol.

Examples of organic acids which can be used in the process of this invention are short chain acids (such as formic, lactic, acetic, propionic, butyric, malic and citric) and medium chain acids (such as caprylic, capric, caproic and lauric).

The present invention is further illustrated by the following examples which are illustrative of certain embodiments designed to teach those of ordinary skill in the art how to practice this invention and to represent the best mode for carrying out this invention.

Example 1

Five animals from each one of 14 bird houses (seven control and seven treated by this process) between 17 and 22 days of age were sacrificed and the live weight and the weight of the livers and the intestines were taken and compared using an analysis of variance correcting for the age of the birds. The composition was 40% cashew nut shell liquid, 12% castor oil and 48% expanded vermiculite. The birds were fed a commercial diet following industry standards. The only difference between the two groups was the supplementation of 0.15% of the composition in the feed.

TABLE 1

| Item | Control | Composition | Difference, % |
|---|---|---|---|
| Body Weight, g | 709 | 737 | 4 |
| Liver, g | 26.10 | 23.25 | 11 |
| Liver, in % of weight[a] | 3.73 | 3.17 | 15 |
| Intestine, g[b] | 51.25 | 48.25 | 6 |
| Intestine, in % of weight[a] | 7.44 | 6.60 | 11 |

[a]Treatments differ $P < 0.05$.
[b]Treatments differ $P = 0.075$.

Table 1 shows that the weight of the intestines and liver as a percentage of total weight was lower for the birds treated by this process. The strength of the data can be checked through the P values. In statistics, a P value tells us the chances that differences attributed to a treatment are actually not due to that treatment but to random variation. In this case, there is less than a 5% chance ($P<0.05$) that the differences in visceral organ mass (liver and intestines) are not due to the process. As the weight of the visceral organs is lower in the treated animals, the weight of the carcass has to be larger and, therefore, there is more saleable meat.

Although one could argue that the treated animals had smaller intestines because of the antimicrobial activity of the composition (a decrease in the microbial challenge results in a decrease of the thickness of the intestines), the weights of the liver are not affected by the antimicrobial activity of the composition as the liver is not directly in contact with the microorganisms as happens with the intestines.

In conclusion, the supplementation of the composition decreased visceral organ mass and, therefore, decreased energy requirements and improved the carcass characteristics of the birds.

Example 2

One hundred and ninety four one day old chicks were divided into two groups. One group was treated with 0.15% of the composition that was 40% cashew nut shell liquid, 12% castor oil and 48% expanded vermiculite, and the other group was used as a control. Each group was divided into 9 repetitions with 33 birds in each repetition. Both groups were fed a diet meeting industry standards, with the only difference between both groups being supplementation of 0.15% of the composition in the feed.

To obtain the apparent metabolizable energy (AME) of the diets, the birds were put in cages and the feces and urine were collected from day 20 to 25. Unlike birds that are on the ground, birds in cages are not challenged by microorganisms, as feces and urine are collected and do not stay in contact with the birds causing pathogenic challenges. Therefore, any increase in AME is due to either a better digestion or to a decrease in maintenance energy requirements.

TABLE 2

| | Diet with Composition | Control Diet | Difference |
|---|---|---|---|
| AME (Kcal/kg)[a] | 2,881 | 2,777 | 4% |
| AME$_n$ (kcal/kg)[a] | 2,568 | 2,449 | 5% |
| FC[b] | 1.772 | 1.806 | 2% |

AMEn = Nitrogen corrected metabolizable energy
FC = Feed conversion (Kg of ingested food/Kg of weight gain)
[a]Treatments differ ($P < 0.06$)
[b]Treatments differ ($P = 0.08$)

Again, as in Example 1, the strength of the data can be checked through the statistics. There is only a 6% chance that the difference in apparent metabolizable energy is not due to the supplementation of the composition, and an 8% chance that the difference in feed conversion is not due to the treatments.

It is important to observe that the increase in energy of the diet in Example 2 is very similar to the increase in weight of the animals of Example 1. A 4% increase in energy is actually higher than what is expected from conventional growth promoters. The industry standard for antibiotic growth promoters is around 2% increase in energy of the diets, which is exactly the improvement observed in feed conversion.

In conclusion, the composition increased the amount of energy efficiency and the feed conversion of the treated animals.

Example 3

Forty eight steers with an initial average weight of 322 kg were divided into two groups and fed until each steer reached 617 kg of live weight. The two groups were treated with Monensin (223 mg/head/day) and the Composition (500 ppm in total feed). Monensin is the antibiotic used in the industry as a standard to affect microbial populations in the rumen of the animals. The change in microbial populations in the rumen shifts the fermentation end products, which results in an improvement in the energy efficiency of the animal. By comparing the Composition to the industry standard, the effects due to changes in microbial populations can be deleted. Therefore, if differences were found between Monensin treated animals and the Composition treated animals, those differences would not arise from the antimicrobial effects, as both products inhibit the same type of bacteria (gram positive). The Composition was 40% cashew nut shell liquid, 12% castor oil and 48% expanded vermiculite.

TABLE 3

| | Monensin | Composition |
|---|---|---|
| Dressing percent | 60[a] | 62[b] |
| Carcass quality grade | 3.18[a] | 4.04[b] |

[a,b]Treatments with different superscripts differ ($P < 0.05$)

Dressing percent is the percentage of the carcass in relation to the total weight of the animal. Carcass quality grade goes from 1 to 9 to indicate, in increasing order, the amount of intramuscular fat. Meats with higher levels of intramuscular fat are more tender and, therefore, more expensive. Also, as the amount of energy found per unit of fat is twice as much as the amount of energy found per unit of carbohydrate and around 40% more than the amount of energy found per unit of protein, meats with more intramuscular fat are more energy dense than leaner meats. Therefore, at equal weights, animals with more intramuscular fat must have been more energy efficient to be able to have more energy dense muscles.

The data in Table 3 shows that the Composition not only increased the amount of carcass, but that the carcass was also more energy dense. In conclusion, the supplementation of the composition increased the energy density of the diet as well as improved the carcass characteristics of the animals.

Therefore, the process of this invention is useful to improve the energy/feed efficiency of the animals and to improve carcass characteristics of animals.

This invention has been described in detail with particular reference to certain embodiments, but variations and modifications can be made without departing from the spirit and scope of the invention as defined in the following claims.

The invention claimed is:

1. A method of decreasing visceral organ mass of an animal as a percentage of total body weight, wherein the method comprises;
    keeping the animal in an environment substantially free of microbial challenge; and
    orally treating the animal with a composition which comprises:
    A. from about 2.0 to about 76.0 percent by weight of at least one triglyceride containing at least one hydroxylated fatty acid having from about 10 to about 20 carbon atoms in its chain and
    B. from about 24.0 to about 95.0 percent by weight of cashew nut shell liquid or a compound selected from the group consisting of cardol, cardanol, anacardic acid and salts of anacardic acid,
    wherein the visceral organ mass of the animal as a percentage of total body weight is decreased in comparison to the animal before treatment.

2. A method as defined by claim 1, wherein the hydroxylated fatty acid is ricinoleic acid, hydroxystearic acid or a blend of ricinoleic acid and hydroxystearic acid.

3. A method as defined by claim 1, wherein the hydroxylated fatty acid is ricinoleic acid.

4. A method as defined by claim 1, wherein the hydroxylated fatty acid is hydroxystearic acid.

5. A method as defined by claim 1, wherein the triglyceride contains ricinoleic acid.

6. A method as defined by claim 1, wherein the triglyceride contains hydroxystearic acid.

7. A method as defined by claim 1, wherein the triglyceride is castor oil.

8. A method as defined by claim 1, wherein the cashew nut shell compound is cardol.

9. A method as defined by claim 1, wherein the cashew nut shell compound is cardanol.

10. A method as defined by claim 1, wherein the cashew nut shell compound is anacardic acid.

11. A method as defined by claim 1, wherein the cashew nut shell compound is a salt of anacardic acid.

12. A method of decreasing visceral organ mass of an animal as a percentage of total body weight, wherein the method comprises:
    keeping the animal in an environment substantially free of microbial challenge; and
    orally treating the animal with a composition which comprises:
    A. from about 2.0 to about 76.0 percent by weight of at least one triglyceride containing at least one hydroxylated fatty acid having from about 10 to about 20 carbon atoms in its chain and
    B. from about 24.0 to about 95.0 percent by weight of cashew nut shell liquid or a compound selected from the group consisting of cardol, cardanol, anacardic acid and salts of anacardic acid,
    wherein the visceral organ mass of the animal as a percentage of total body weight is decreased in comparison to the animal before treatment and wherein the ratio of component A:component B is from about 1:4 to about 1:2.

13. A method as defined by claim 12, wherein the hydroxylated fatty acid is ricinoleic acid, hydroxystearic acid, or a blend of ricinoleic acid and hydroxystearic acid.

14. A method as defined by claim 12, wherein the hydroxylated fatty acid is ricinoleic acid.

15. A method as defined by claim 12, wherein the hydroxylated fatty acid is hydroxystearic acid.

16. A method as defined by claim 12, wherein the triglyceride contains ricinoleic acid.

17. A method as defined by claim 12, wherein the triglyceride contains hydroxystearic acid.

18. A method as defined by claim 12, wherein the triglyceride is castor oil.

19. A method as defined by claim 12, wherein the cashew nut shell compound is cardol.

20. A method as defined by claim 12, wherein the cashew nut shell compound is cardanol.

21. A method as defined by claim 12, wherein the cashew nut shell compound is anacardic acid.

22. A method as defined by claim 12, wherein the cashew nut shell compound is a salt of anacardic acid.

23. A method of decreasing visceral organ mass of an animal as a percentage of total body weight, wherein the process comprises;
    keeping the animal in an environment substantially free of microbial challenge; and
    orally treating the animal with a composition which comprises:
    A. from about 2.0 to about 76.0 percent by weight of at least one triglyceride containing at least one hydroxylated fatty acid having from about 10 to about 20 carbon atoms in its chain and
    B. from about 24.0 to about 95.0 percent by weight of cashew nut shell liquid or a compound selected from the group consisting of cardol, cardanol, anacardic acid and salts of anacardic acid, and
    C. a feed carrier
    wherein the visceral organ mass of the animal as a percentage of total body weight is decreased in comparison to the animal before treatment and wherein the composition is present in an amount of about 10 to about 10,000 parts per million of the feed carrier.

24. A method as defined by claim 23, wherein the hydroxylated fatty acid is ricinoleic acid, hydroxystearic acid or a blend of ricinoleic acid and hydroxystearic acid.

25. A method as defined by claim 23, wherein the hydroxylated fatty acid is ricinoleic acid.

26. A method as defined by claim 23, wherein the hydroxylated fatty acid is hydroxystearic acid.

27. A method as defined by claim 23, wherein the triglyceride contains ricinoleic acid.

28. A method as defined by claim 23, wherein the triglyceride contains hydroxystearic acid.

29. A method as defined by claim 23, wherein the triglyceride is castor oil.

30. A method as defined by claim 23, wherein the cashew nut shell compound is cardol.

31. A method as defined by claim 23, wherein the cashew nut shell compound is cardanol.

32. A method as defined by claim 23, wherein the cashew nut shell compound is anacardic acid.

33. A method as defined by claim 23, wherein the cashew nut shell compound is a salt of anacardic acid.

* * * * *